United States Patent [19]

Ivansons et al.

[11] Patent Number: 5,525,186
[45] Date of Patent: Jun. 11, 1996

[54] WAFER FOR USE IN THE SELECTIVE CONNECTING AND DISCONNECTING OF PLASTIC TUBES

[75] Inventors: Ivars V. Ivansons, Newark; Valdis Ivansons; Dudley W. C. Spencer, both of Wilmington, all of Del.

[73] Assignee: Denco, Inc., Wilmington, Del.

[21] Appl. No.: 290,548

[22] Filed: Aug. 15, 1994

Related U.S. Application Data

[63] Continuation-in-part of Ser. No. 158,505, Nov. 29, 1993, Pat. No. 5,397,425, which is a continuation-in-part of Ser. No. 139,833, Oct. 22, 1993, abandoned, which is a continuation-in-part of Ser. No. 965,875, Oct. 23, 1992, Pat. No. 5,279,685, which is a continuation-in-part of Ser. No. 764,249, Sep. 23, 1991, Pat. No. 5,209,800, which is a continuation-in-part of Ser. No. 682,977, Apr. 10, 1991, Pat. No. 5,156,701, which is a continuation-in-part of Ser. No. 604,967, Oct. 29, 1990, abandoned, which is a continuation-in-part of Ser. No. 569,855, Aug. 20, 1990, Pat. No. 5,141,592.

[51] Int. Cl.$^6$ ........................... B29C 35/02
[52] U.S. Cl. .................. 156/503; 156/352; 156/359; 156/499; 156/535; 116/217; 374/160
[58] Field of Search ................ 156/304.2, 304.5, 156/304.6, 352, 353, 502, 503, 508, 518, 530, 535, 499, 359, 64; 116/217; 374/160

[56] References Cited

U.S. PATENT DOCUMENTS

| | | | |
|---|---|---|---|
| 3,299,275 | 1/1967 | Green et al. | 374/160 X |
| 3,729,360 | 4/1973 | McElroy | 156/535 X |
| 3,793,119 | 2/1974 | Province | 156/535 X |
| 4,516,520 | 5/1985 | Whaley | 116/217 |

FOREIGN PATENT DOCUMENTS

| | | | |
|---|---|---|---|
| 2239727 | 2/1975 | France | 116/217 |

*Primary Examiner*—David A. Simmons
*Assistant Examiner*—Paul M. Rivard
*Attorney, Agent, or Firm*—Connolly & Hutz

[57] ABSTRACT

A wafer is used in a device for the selective connecting and disconnecting of plastic tubes. The wafer is in the form of a heated plate having an outwardly extending scoop on each side thereof. The wafer also includes a generally straight line horizontal slit extending through the plate from the trailing downstream edge inwardly. In order to assure single use usage of the wafer, an aperture is provided through the wafer with the aperture being covered by a sensing material. A sensor in the device will inactivate the device if the sensing material is not detected.

35 Claims, 3 Drawing Sheets

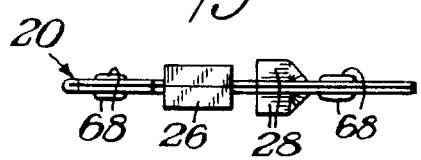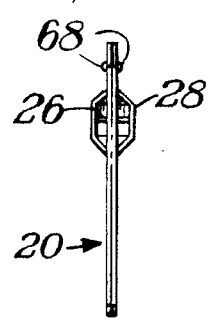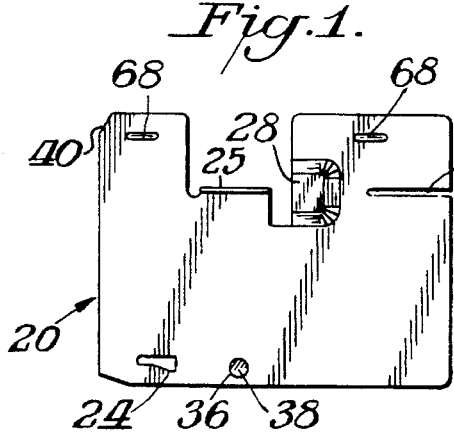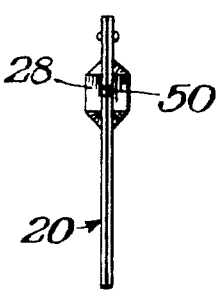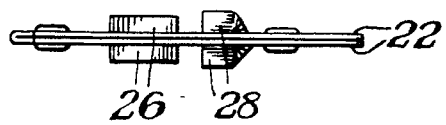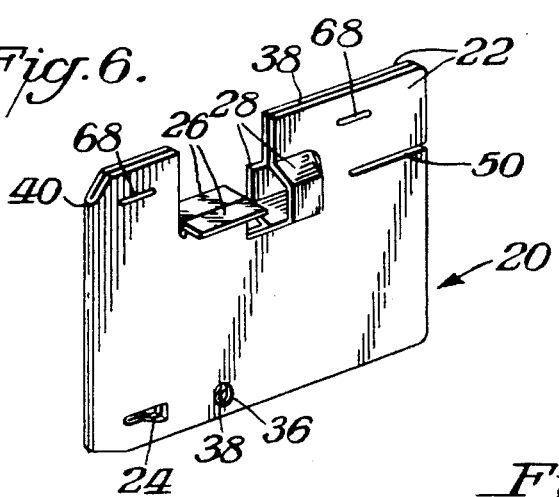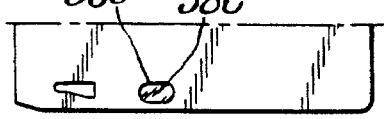

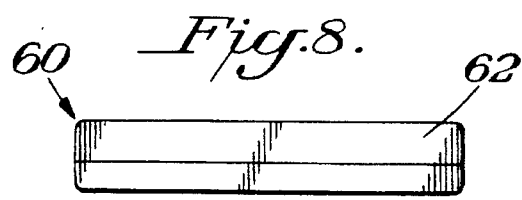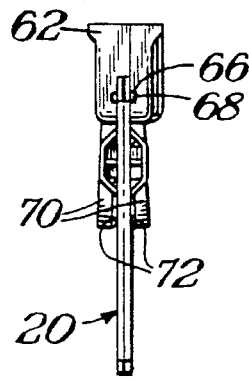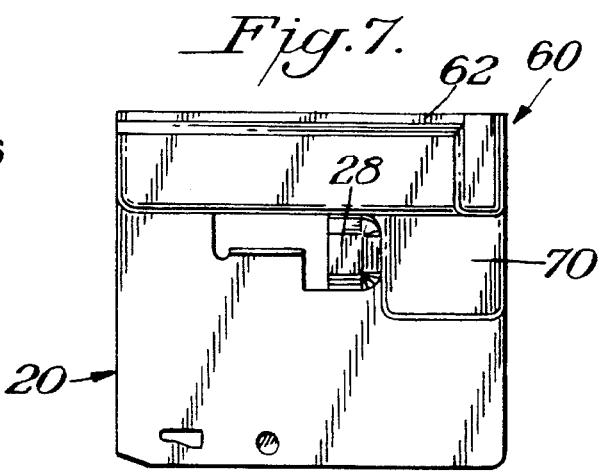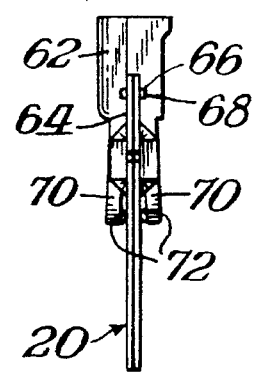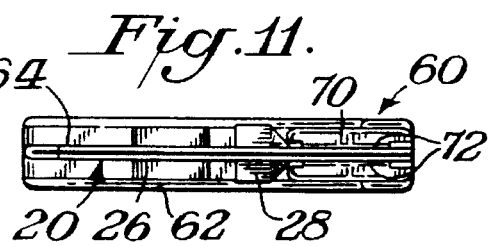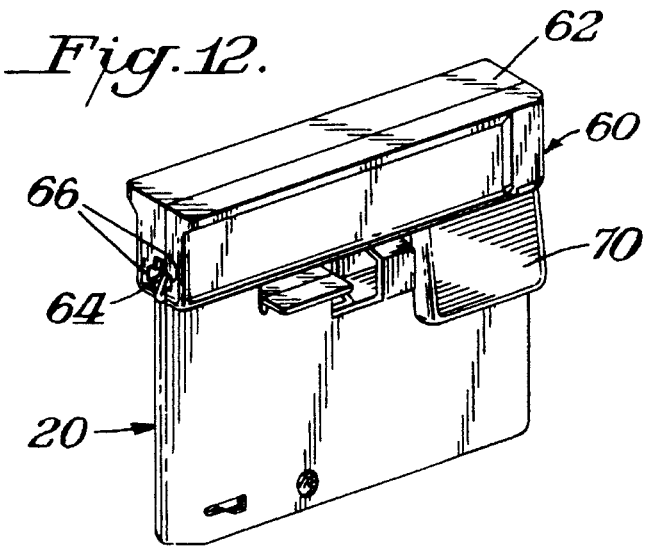

WAFER FOR USE IN THE SELECTIVE CONNECTING AND DISCONNECTING OF PLASTIC TUBES

CROSS-REFERENCE TO RELATED APPLICATIONS

This application is a continuation-in-part of application Ser. No. 158,505, filed Nov. 29, 1993, now U.S. Pat. No. 5,397,425, which in turn is a continuation-in-part of Ser. No. 139,833, filed Oct. 22, 1993 now abandoned, which in turn is a continuation-in-part of application Ser. No. 965,875 filed Oct. 23, 1992, now U.S. Pat. No. 5,279,685, which in turn is a continuation-in-part of application Ser. No. 764,249 filed Sep. 23, 1991, now U.S. Pat. No. 5,209,800, which in turn is a continuation-in-part of application Ser. No. 682,977 filed Apr. 10, 1991, now U.S. Pat. No. 5,156,701, which in turn is a continuation-in-part of application Ser. No. 604,967 filed Oct. 29, 1990, now abandoned, which in turn is a continuation-in-part of application Ser. No. 569,855 filed Aug. 20, 1990, now U.S. Pat. No. 5,141,592.

BACKGROUND OF THE INVENTION

The present invention is directed to the total containment welding of plastic tubes. Various prior art exists disclosing different approaches for welding plastic tubes together. Prior patents disclose processes where the weld connection depends on the melt rheology of plastic resulting in non-uniform size of the weld connection. No attempt was made in the prior art to gain control of the size of the weld connection.

Parent application Ser. No. 158,505 discloses various wafer constructions for use in the total containment welding of plastic tubes and in the selective connect and disconnect of the plastic tubes. Such wafers are sufficiently effective that the same wafer could be used multiple times by removing the plastic material accumulated on the wafer after each use. In certain applications, however, it is desired to prevent the multiple use of the wafer and to assure that the wafer will be used only once.

SUMMARY OF THE INVENTION

An object of this invention is to provide a wafer of the type disclosed in parent application Ser. No. 158,505 wherein there is assurance that the wafer can only be used once.

It is a further object of this invention to provide such a wafer which is capable of inactivating the total containment device where the wafer mounted in the device has previously been used.

In accordance with this invention the wafer is preferably generally of the type disclosed in parent application Ser. No. 158,505 in that it is in the form of a flat plate having opposite sides, each of which is disposed toward a respective set of first and second clamp jaws. Each of the sides of the wafer has an outwardly extending scoop generally located in the plane between the first and second clamp jaws for removing plastic material from the plastic tube as the wafer moves through the gap to control the size of the weld connection. The wafer in the preferred practice of this invention also includes an aperture or hole extending completely therethrough. The aperture is covered with a sensing material. The total containment welding device includes a sensor for sensing the material. If the material is not sensed the device is inactivated. A material is selected which preferably is removed during operation of the device so that after a single use the aperture is no longer covered by the material.

The wafer may be provided with more than one aperture each of which has detector material. A more sophisticated sensing would be required to assure that all of the apertures are provided with the material. In another practice of the invention the hole or aperture may be an elongated slot having some indicia, such as a bar code, which could be visible to the naked eye or could be invisible and be capable of being sensed by the device.

BRIEF DESCRIPTION OF THE DRAWINGS

FIG. 1 is a side elevational view of a wafer in accordance with this invention;

FIGS. 1A and 1B are side elevational views of a portion of a wafer similar to that of FIG. 1 showing alternate practices of this invention;

FIG. 2 is a top plan view of the wafer shown in FIG. 1;

FIGS. 3 and 4 are front and rear elevational views of the wafer shown in FIGS. 1–2;

FIG. 5 is a bottom plan view of the wafer shown in FIGS. 1–4;

FIG. 6 is a perspective view of the wafer shown in FIGS. 1–5;

FIG. 7 is a side elevational view showing the wafer of FIGS. 1–6 mounted in a holder;

FIG. 8 is a top plan view of the holder/wafer shown in FIG. 7;

FIGS. 9 and 10 are front and rear elevational views of the wafer/holder shown in FIGS. 7–8;

FIG. 11 is a bottom plan view of the wafer/holder shown in FIGS. 7–10;

FIG. 12 is a perspective view of the wafer/holder shown in FIGS. 7–11;

DETAILED DESCRIPTION

Figure 13:
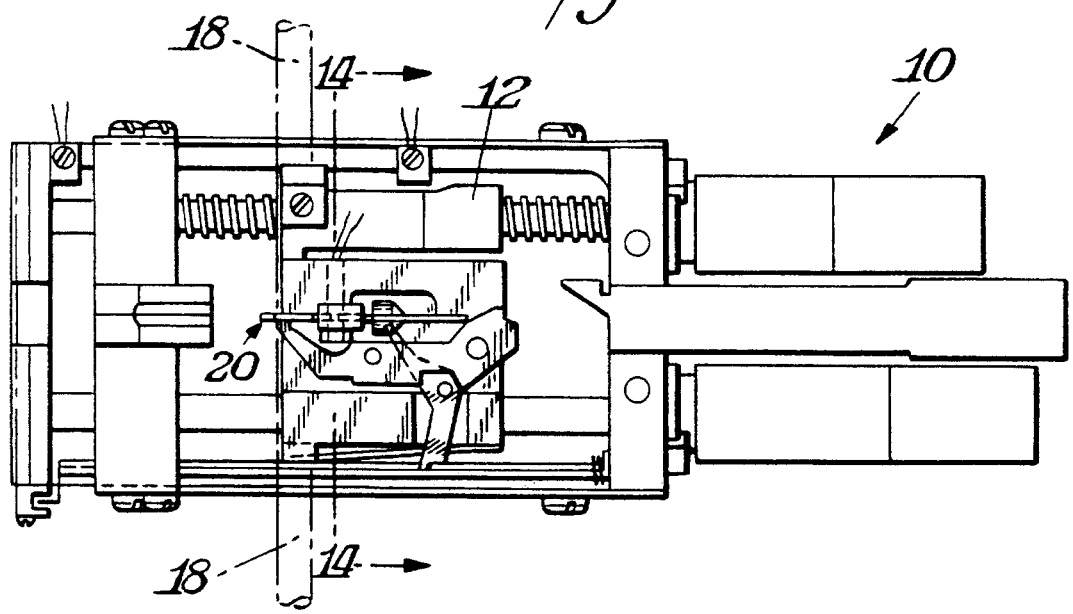
FIG. 13 is a top plan view of a portion of a total containment device in which the wafer of FIGS. 1–12 could be used.

The present invention is directed to variations of the wafer shown and described in parent application Ser. No. 158,505, the details of which are incorporated herein by reference thereto. Such wafer could advantageously be used in a total containment device of the type described in parent U.S. Pat. No. 5,279,685. The details of the '685 parent patent and of the other parent patents and applications are all incorporated herein by reference thereto.

The present invention includes features in the wafer to assure single use of a wafer. Advantageously, the preferred practice of this invention requires minimal modifications to the wafer and total containment device.

FIGS. 1–6 show the details of wafer 20. As shown therein wafer 20 is in the form of a flat plate having a pair of opposite sides 22,22. Wafer 20 also includes a cut-out or notch 24 for engagement by a pawl in the home position of the wafer in the manner described in parent U.S. Pat. No. 5,279,685. Wafer 20 also includes a pair of wings 26 as described in the various parent applications.

Wafer 20 is unique in that it also includes a scoop 28 on each of its sides. Scoop 28 is located generally in line with wings 26 which would be at an elevation which is in the general plane of the clamped tubes 18 where each upper jaw and lower jaw press against the tube ends to flatten the tube ends. See FIG. 13 and U.S. Pat. No. 5,279,685. Thus, scoops 28 are in a position to contact the melted tubes.

The wafer 20 also includes a slit 50 extending completely through the wafer downstream from scoops 28. As illustrated slit 50 extends inwardly from the downstream generally vertical trailing edge in a straight line generally horizontal direction toward the upstream generally vertical leading edge of wafer 20. Slit 50 terminates downstream from scoops 28. Slit 50 may be of any suitable dimension and preferably has a length of 7 mm and a width of 0.5 mm. Slit 50 is disposed in line with scoop 28 and wing 26 on each of the sides 22 of wafer 20.

The advantage of providing a slit, such as slit 50, in the heated wafer downstream from the scoops 28 is to permit the molten material from the tubes 18 to begin contacting each other at an earlier time while the tubes are still in the area of the heated wafer.

In order to assure the single use of the wafer, wafer 20 is provided with a hole or aperture 36 at any suitable location such as being generally in line with notch 24. Aperture 36 is intended to be covered by a sensing material 38. This can be conveniently accomplished by forming the wafer as a plate which is folded upon itself at one end 40 so that the wafer 20 is of double thickness, as best shown in FIGS. 2 and 4–6. Prior to the complete folding the sensing material 38 is positioned to cover hole 36. Material 38 is preferably selected to be of material which would melt or otherwise be destroyed upon the heating of the wafer. Thus, once there has been a single use of the wafer, material 38 no longer covers aperture 36 and can not be sensed in an attempted second use of the wafer.

Figure 14:
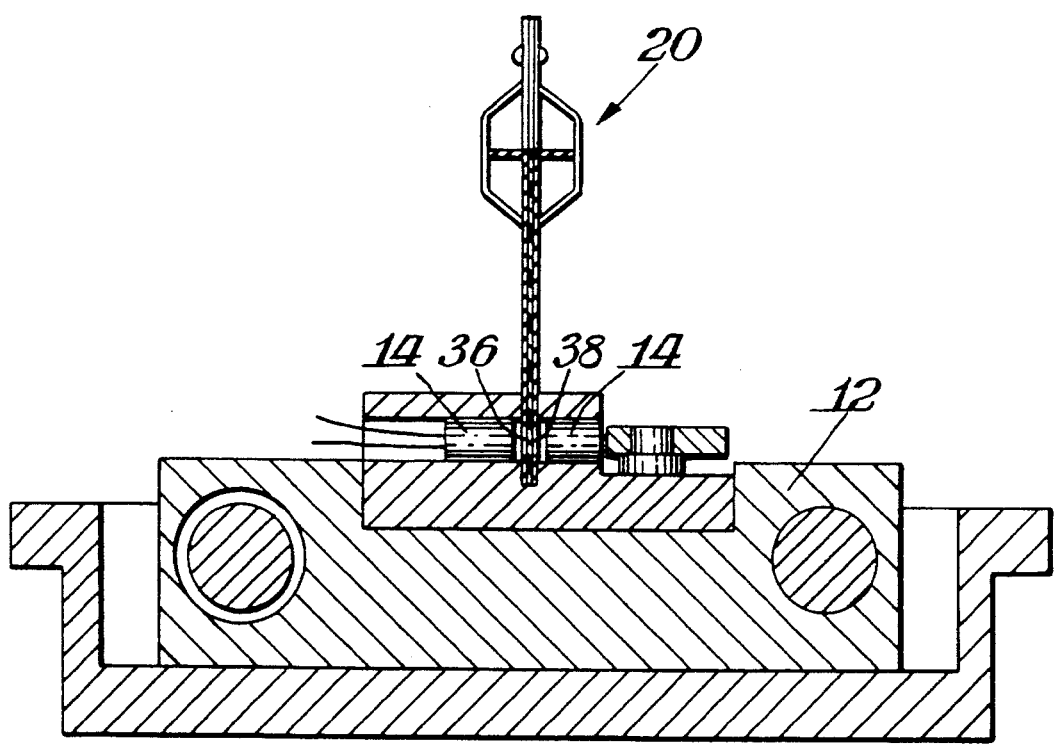
FIG. 14 is a cross-sectional view taken through FIG. 13 along the line 14—14.

FIGS. 13–14 illustrate, in general, portions of the total containment device 10 of the type described in parent U.S. Pat. No. 5,279,685. As shown therein device 10 includes a carriage 12 for moving the wafer through the device. Parent U.S. Pat. No. 5,279,685 discloses the inclusion of various sensors, such as for indicating that the wafer is properly loaded in the carriage and for detecting that the wafer is properly conditioned with respect to the clenching block. FIG. 14 illustrates one such sensor 14 which, in the device of the parent patent, functions as the aperture blockage sensor. Sensor 14 is mounted in the path of movement of aperture 36 and thus would sense aperture 36 passing through the path of view of sensor 14. Thus, the present invention advantageously makes use of a sensor already in device 10 for its single use sensing operation. If desired, however, one of the other sensors or a completely additional sensor may be used for this purpose.

In operation, as wafer 20 is moved in a downstream direction sensor 14 views aperture 36. If there is sensing material 38 located in aperture 36 the material will be sensed. Such sensing could be in terms, for example, of a voltage reading which would differ from the voltage reading of the copper wafer material 20 and would differ from the voltage reading of a completely open hole 36. If the sensor 14 does not detect the proper voltage which would result from the proper sensing material 38 being in aperture 36 then the device 10 would be inactivated. This would mean that either the wafer 20 had been previously used and no longer has sensing material 38 or that there is a manufacturing defect and the sensing material was not mounted over hole 36.

When the sensing material 38 is properly detected and other device requirements are met, the wafer 20 is heated for use in the selective connect/disconnect of the plastic tubes 18,18. The heating operation results in a melting of sensing material 38 so that hole 36 is completely exposed.

The concept of sensing a condition of the wafer which would indicate whether or not the wafer has been previously used can be practiced in various manners. FIG. 1A, for example, illustrates the provision of two holes 36A,36B, each with a sensing material 38A,38B. Sensing materials 38A and 38B may be the same or different materials. This arrangement would provide a more sophisticated reading to require a binary or sequential voltage reading from sensor 14 in order to prevent device 10 from being inactivated. Such more sophisticated reading would be desirable to make it more difficult for a user to attempt to insert sensing material back into wafer 20 after the wafer has already been used.

Cover material 38 is preferably a two mil thick polyethylene sheet which may contain carbon black. Such material could also be used as material 38A. Material 38B could likewise be the same material or could be a material having a different voltage characteristic.

FIG. 1B shows yet another practice of this invention wherein the aperture 36C is an elongated slot. The cover material 38C could be the same as cover material 38 or could simply be any suitable material, preferably a transparent material having some indicia thereon which would be detected by the sensor. For example, the indicia could be a bar code or some form of alphanumeric code. The indicia could be visible to the naked eye or could be invisible to the naked eye since it is only necessary that the indicia be visible to the sensor.

FIGS. 7–12 illustrate wafer 20 mounted in a suitable holder 60 which could be of the same general construction as the holder illustrated in FIG. 14 of parent U.S. Pat. No. 5,279,685. The purpose of the holder is to mount wafer in the carriage, during the initial movement of wafer 20. Holder 16 generally includes a split body 62 having a slot 64 into which wafer 20 would be slidably mounted. Interior of body 62 would include two registration recesses for receiving lugs 68 on wafer 20. Holder body 62 includes downward extensions 70 which have half round filets 72 to increase the frictional contact on wafer 20 by the spring action of the body extension 70 which thus act as spring arms.

In operation, wafer 20 would be mounted in holder 60 during the initial positioning of the wafer in carriage 12. As the wafer is moved downstream it is detached from holder 60 thereby exposing slit 50 which is initially covered by extension 70 of holder 60.

It is to be understood that the holder 60 illustrated in FIGS. 7–12 may be used with the type of wafer described in parent application Ser. No. 158,505 and is not limited to the type of wafer intended for single use purpose. Even where holder 60 is used for a single use wafer, the holder itself may be reused multiple times.

What is claimed is:

1. A wafer for use in a device for selectively connecting and disconnecting plastic tubes, said wafer being in the form of a heatable flat plate having opposite sides, an aperture extending completely through said sides, a sensing material located within said aperture, and said sensing material having different physical characteristics than said sides and said aperture whereby a sensor located in the path of movement of said aperture during the movement of said wafer causes the sensor to detect the presence of said sensing material at said aperture.

2. The wafer of claim 1 wherein said sensing material includes indicia thereon to permit said indicia to be sensed.

3. The wafer of claim 1 wherein said sensing material is meltable upon the heating of said wafer whereby said sensing material melts after a single use of said wafer.

4. The wafer of claim 3 wherein said sensing material is plastic, and said plate is made from metal.

5. The wafer of claim 1 wherein said aperture is a first aperture, said sensing material being a first sensing material, a second aperture extending completely through said sides, and a second sensing material covering said second aperture.

6. The wafer of claim 5 wherein said first aperture and said second aperture are aligned with each other.

7. The wafer of claim 5 wherein said first sensing material and said second sensing material have different sensing characteristics.

8. The wafer of claim 1 wherein said aperture is an elongated slot.

9. The wafer of claim 8 wherein said sensing material includes a bar code.

10. A wafer for use in a device for selectively connecting and disconnecting plastic tubes, said wafer being in the form of a heatable flat plate having opposite sides, an aperture extending completely through said sides, a sensing material covering said aperture, said sensing material having different physical characteristics than said sides and said aperture whereby a sensor located in the path of movement of said aperture during the movement of said wafer causes the sensor to detect the presence of said sensing material at said aperture, said flat plate being folded upon itself to create said opposite sides, and said sensing material being inserted between said sides.

11. A wafer for use An a device for selectively connecting and disconnecting plastic tubes, said wafer being in the form of a heatable flat plate having opposite sides, an aperture extending completely through said sides, a sensing material covering said aperture, said sensing material having different physical characteristics than said sides and said aperture whereby a sensor located in the path of movement of said aperture during the movement of said wafer causes the sensor to detect the presence of said sensing material at said aperture, a scoop extending outwardly from each of said sides, each of said scoops having an open end and otherwise being closed to form a collecting pocket, and each of said scoops being located at the same portion of its respective side as the other of said scoops whereby said scoops form mirror images of each other.

12. The wafer of claim 11 including a wing extending outwardly from each of said sides spaced from and generally in line with a respective one of said scoops.

13. The wafer of claim 12 wherein said scoops and said wings are located at the upper end of each of said sides, and a notch being formed in the lower end of said wafer.

14. The wafer of claim 13 including a generally straight line slit extending from an edge of said plate completely through said plate, and said slit being generally in line with and downstream from said scoops.

15. A wafer for use in a device for selectively connecting and disconnecting plastic tubes, said wafer being in the form of a heatable flat plate having opposite sides, an aperture extending completely through said sides, a sensing material covering said aperture, said sensing material having different physical characteristics than said sides and said aperture whereby a sensor located in the path of movement of said aperture during the movement of said wafer causes the sensor to detect the presence of said sensing material at said aperture, a generally straight line slit extending from an edge of said plate completely through said plate, and said slit being generally in line with and downstream from said scoops.

16. The wafer of claim 12 including a wing extending outwardly from each of said sides spaced from and generally in line with a respective one of said scoops.

17. A wafer for use in a device for selectively connecting and disconnecting plastic tubes, said wafer being in the form of a heatable flat plate having opposite sides, an aperture extending completely through said sides, a sensing material covering said aperture, said sensing material having different physical characteristics than said sides and said aperture whereby a sensor located in the path of movement of said aperture during the movement of said wafer causes the sensor to detect the presence of said sensing material at said aperture, in combination therewith, a holder, said wafer having upper and lower edges, said holder having an elongated slot, said wafer being detachably inserted into said slot at one of said edges, and said wafer being unsupported from said holder outwardly toward the other of said edges.

18. The wafer of claim 17 wherein said holder and said wafer include retainer elements.

19. A wafer for use in a device for selectively connecting and disconnecting plastic tubes, said wafer being in the form of a heatable flat plate having opposite sides, an aperture extending completely through said sides, a sensing material covering said aperture, said sensing material having different physical characteristics than said sides and said aperture whereby a sensor located in the path of movement of said aperture during the movement of said wafer causes the sensor to detect the presence of said sensing material at said aperture, in combination therewith, a holder, said holder having an elongated slot, said wafer being detachably inserted into said slot, said holder and said wafer including retainer elements, said retainer elements comprise lugs extending outwardly from said sides and recesses in said holder, and said holder being made of a resilient material to form a spring like mounting of said wafer in said holder.

20. A wafer for use in a device for selectively connecting and disconnecting plastic tubes, said wafer being in the form of a heatable flat plate having opposite sides, an aperture extending completely through said sides, a sensing material covering said aperture, said sensing material having different physical characteristics than said sides and said aperture whereby a sensor located in the path of movement of said aperture during the movement of said wafer causes the sensor to detect the presence of said sensing material at said aperture, in combination with a weld/disconnect device which includes means for moving said wafer in a downstream direction, and a sensor in said device having a line of view disposed in the path of movement of said aperture.

21. The wafer of claim 20 wherein said sensor inactivates said device upon the detection of the absence of said sensing material in said aperture.

22. A wafer for use in a device for selectively connecting and disconnecting plastic tubes, said wafer being in the form of a heated flat plate having opposite sides, each of said sides having an outwardly extending scoop, each of said scoops having an open end and otherwise being closed to form a collecting pocket, and each of said scoops being located at the same portion of its respective side as the other of said scoops whereby said scoops form mirror images of each other.

23. The wafer of claim 22 including a wing extending outwardly from each of said sides spaced from and generally in line with a respective one of said scoops.

24. The wafer of claim 23 wherein said scoops and said wings are located at the upper end of each of said sides, and a notch being formed in the lower end of said wafer.

25. The wafer of claim 24 including a generally straight line slit extending from an edge of said plate completely through said plate, and said slit being generally in line with and downstream from said scoops.

26. The wafer of claim 22 including a generally straight line slit extending from an edge of said plate completely through said plate, and said slit being generally in line with and downstream from said scoops.

27. The wafer of claim 22 including an aperture extending completely through said plate, and a sensing material covering said aperture.

28. In a wafer for use in a device for selectively connecting and disconnecting plastic tubes, in combination with means for moving said wafer in a downstream direction, said wafer being in the form of a heated flat plate having opposite sides and having a leading upstream generally vertical edge and a trailing downstream generally vertical edge, the improvement being in that a generally straight line horizontal slit extends completely through said plate from said trailing downstream edge inwardly.

29. The wafer of claim 28 wherein said slit is about 7 mm long and about 0.5 mm wide.

30. The wafer of claim 29 including a wing extending outwardly from each of said sides spaced upstream from and generally in line with said slit.

31. The wafer of claim 30 including a scoop extending outwardly from each of said sides generally in line with and between said slit and said wings.

32. The wafer of claim 28 including an aperture extending completely through said plate, and a sensing material covering said aperture.

33. A wafer for use in a device for selectively connecting and disconnecting plastic tubes, said wafer being in the form of a heatable flat plate having opposite sides, an aperture extending completely through said sides, a sensing material covering said aperture, said sensing material being of substantially lesser area than the area of said plate, said sensing material being generally confined to said aperture, substantially all of said sides of said flat plate being exposed, and said sensing material having different physical characteristics than said sides and said aperture whereby a sensor located in the path of movement of said aperture during the movement of said wafer causes the sensor to detect the presence of said sensing material at said aperture.

34. The wafer of claim 12 wherein said sensing material is confined below the surface of said plate.

35. The wafer of claim 33 wherein said sensing material is meltable upon the heating of said wafer whereby said sensing material melts after a single use of said wafer.

* * * * *